United States Patent
Satoh et al.

(10) Patent No.: US 7,034,288 B2
(45) Date of Patent: Apr. 25, 2006

(54) TIME-OF-FLIGHT MASS SPECTROMETER

(75) Inventors: Takaya Satoh, Tokyo (JP); Yoshihiro Kammei, Tokyo (JP); Tatsuji Kobayashi, Tokyo (JP); Mitsuyasu Iwanaga, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 10/877,497

(22) Filed: Jun. 25, 2004

(65) Prior Publication Data

US 2005/0023458 A1 Feb. 3, 2005

(51) Int. Cl.
*B01D 59/44* (2006.01)
*H01J 49/00* (2006.01)

(52) U.S. Cl. .................. 250/287; 250/287; 250/281
(58) Field of Classification Search .............. 250/281, 250/282, 287, 288
See application file for complete search history.

(56) References Cited

U.S. PATENT DOCUMENTS

| 5,763,878 | A  | * | 6/1998 | Franzen ............... 250/292 |
| 6,294,780 | B1 | * | 9/2001 | Wells et al. ........... 250/288 |
| 6,515,279 | B1 | * | 2/2003 | Baykut ................. 250/285 |
| 6,600,155 | B1 | * | 7/2003 | Andrien et al. ........ 250/287 |

FOREIGN PATENT DOCUMENTS

| JP | 52-087086 | 7/1977 |
| JP | 62-168328 | 7/1987 |

* cited by examiner

*Primary Examiner*—John R. Lee
*Assistant Examiner*—Jennifer Yantomo
(74) *Attorney, Agent, or Firm*—The Webb Law Firm

(57) ABSTRACT

A time-of-flight mass spectrometer capable of cutting out a major portion of carrier gas-derived ions ahead of the ion reservoir. The ion source is of the electron impact type and has source magnets for deflecting some of the produced ions away from the center axis of the ion reservoir. Electrostatic lenses for promoting the deflection of the ions caused by the source magnets and a differentially pumped slit for cutting off the deflected ions are mounted downstream of the ion source.

9 Claims, 4 Drawing Sheets

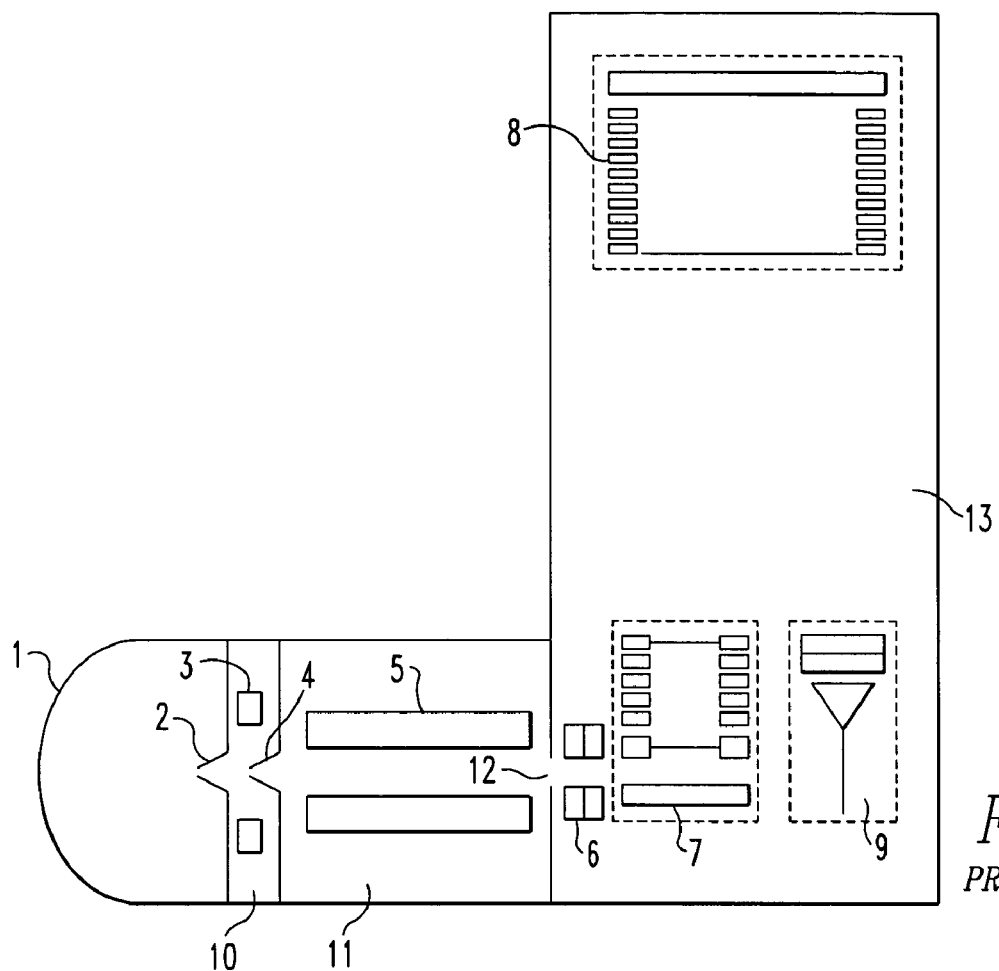
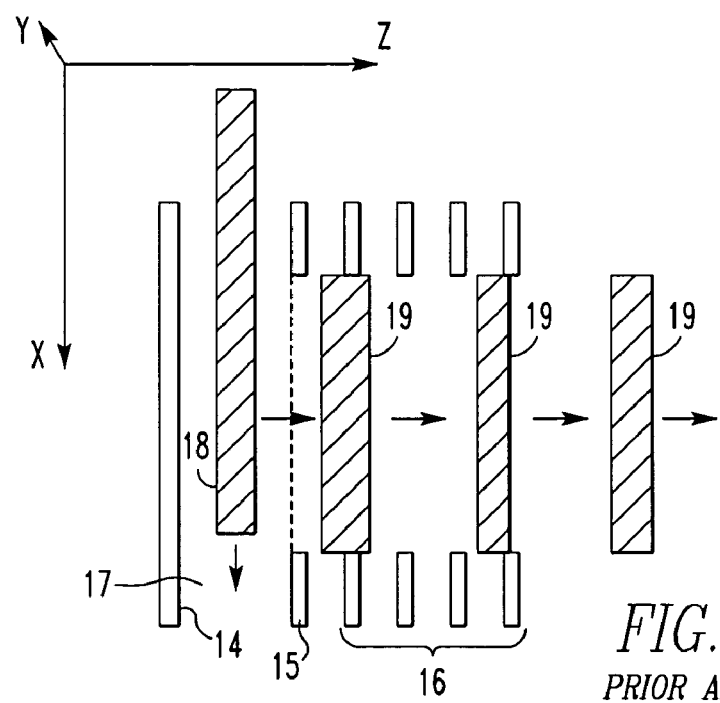
FIG.1
PRIOR ART
FIG.2
PRIOR ART

TIME-OF-FLIGHT MASS SPECTROMETER

BACKGROUND OF THE INVENTION

1. Field of the Invention

The present invention relates to a high-performance gas chromatograph/mass spectrometer used for quantitative analysis and simultaneous qualitative analysis of trace organic compounds and for structural analysis of sample ions.

2. Description of Related Art

Gas chromatograph/mass spectrometer (GC-MS) instruments fitted with electron impact (EI) ion sources chiefly include magnetic-sector and quadrupole mass spectrometers.

In a magnetic-sector mass spectrometer, a high ion acceleration voltage of the order of kilovolts is usually applied to ions produced in an EI ion source to make them travel toward the mass analyzer region. The ions pass through a free space or a lens system, such as Q lenses, and then are deflected in the mass analyzer region based on the following relation:

$$m/z = K \cdot B^2 / V_a$$

where m/z is the mass-to-charge ratio of the ions, B is the magnetic flux density of the magnetic field, $V_a$ is the ion acceleration voltage, and K is a constant.

Accordingly, if the magnetic flux density B is kept at a certain value, and if only ions having a certain mass-to-charge ratio are allowed to reach the detector, then a quantitative analysis of the ions can be performed. Furthermore, if the magnetic flux density B is swept, a mass spectrum can be obtained. Hence, simultaneous qualitative analysis can be performed.

On the other hand, in a quadrupole mass spectrometer, ions produced in an EI ion source are made to travel under a low acceleration voltage of about tens of volts. The mass analyzer region of the quadrupole mass spectrometer literally consists of four parallel metal rods which may have hyperbolic or cylindrical surfaces. A superimposition of an RF AC voltage and a DC voltage is applied to each rod to perform mass separation. Based on the following relation, only ions having a certain mass-to-charge ratio pass through the mass analyzer region:

$$m/z = K \cdot V_f / f^2$$

where m/z is the mass-to-charge ratio of the ions, $V_f$ is the RF amplitude voltage, f is the RF frequency, and K is a constant.

In each of the magnetic-sector and quadrupole mass spectrometers, the EI ion source consists of an ionization chamber, source magnets, a filament, and an Einzel lens system made up of plural electrodes. Each of the Einzel lens electrodes is made of a unitary structure provided with a circular opening about the axis of the ion trajectory. See Japanese Patent Laid-Open No. S62-168328.

In recent years, a gas chromatograph/time-of-flight mass spectrometer fitted with an EI ion source has been developed. This instrument has an analyzer region made of an orthogonal acceleration time-of-flight (oa-TOF) mass spectrometer. A time-of-flight mass spectrometer performs mass separation by making use of the fact that the flight speed differs according to the ion mass when a given acceleration voltage is applied to ions. A mass spectrum is recorded according to differences in arrival time at the ion detector.

As this ion detector, a microchannel plate (MCP) detector having high time resolution is often used. In the case of an oa-TOFMS instrument, ions introduced into the ion acceleration region all reach the ion detector regardless of their mass-to-charge ratio.

Therefore, if a carrier gas, such as helium gas, that flows in at a high flow rate of 1 to 2 ml per min. from a gas chromatograph is ionized in large quantity by electron impact, the amount of the resulting ion current reaches 100 to 1,000 times the amount of ion current of the sample ions.

When this large amount of carrier gas ions reaches the MCP, a dead time of tens of microseconds to several milliseconds is produced due to saturation of the MCP. As a result, mass spectral data is lost. In addition, other problems, such as shortening of the life of the MCP, take place.

In conventional magnetic-sector and quadrupole mass spectrometers, only ions having a certain mass-to-charge ratio are allowed to reach the detector, and mass separation is effected. Because of this mechanism, it has been possible to prevent the ions of the carrier gas of the gas chromatograph from reaching the detector by appropriately setting the analytical conditions. Therefore, it can be understood that these problems are unique to TOFMS instruments. Furthermore, where ions are treated under low acceleration conditions, the effects of charging due to adhesion of contaminants to the electrodes cannot be neglected.

For example, FIG. 1 shows the configuration of an orthogonal acceleration time-of-flight mass spectrometer. This instrument has an external ion source 1, a differentially pumped (evacuated) chamber 10 formed by first and second partition walls and by a vacuum pump (not shown), an intermediate chamber 11, and a measuring chamber 13. A first orifice 2 is formed in the first partition wall of the differentially pumped chamber 10. A ring lens 3 is placed in the differentially pumped chamber 10. A second orifice 4 is formed in the second partition wall of the differentially pumped chamber 10. Ion guides 5 are placed in the intermediate chamber 11. Ion optics including a set of lenses 6 made up of focusing lenses and a deflector, a launcher 7 consisting of an ion repeller plate and accelerating lenses (grids), an ion reflector 8 for reflecting ions, and an ion detector 9 are fitted in the measuring chamber 13.

In this configuration, ions produced from a sample in the external ion source 1 are first introduced into the differentially pumped chamber 10 through the first orifice 2. The ions that tend to diffuse themselves in the differentially pumped chamber 10 are focused by the ring lens 3 located inside the chamber 10 and admitted into the intermediate chamber 11 through the second orifice 4. The ions are then decreased in kinetic energy in the intermediate chamber 11. The diameter of the ion beam is reduced by the RF electric field produced by the ion guides 5 and guided into the high-vacuum measuring chamber 13. A third orifice 12 is formed in the partition wall that partitions the intermediate chamber 11 and measuring chamber 13 from each other. The ions guided in from the ion guides 5 are shaped into a round ion beam having a certain diameter by the third orifice 12 and introduced into the measuring chamber 13.

The set of lenses 6 consisting of the focusing lenses and deflector is installed at the entrance of the measuring chamber 13. The ion beam entering the measuring chamber 13 is corrected in terms of diffusion and deflection by the lenses 6 and then introduced into the launcher 7. As shown in FIG. 2, an ion reservoir and accelerating lenses arrayed perpendicularly to the axis of the ion reservoir are mounted in the launcher 7. In the ion reservoir, an ion repeller electrode 14 and grid 15 are placed opposite to each other.

The ion beam 18 is at first in a very low energy state of 20 to 50 eV and is introduced parallel toward the ion reservoir 17 surrounded by the ion repeller electrode 14, grids 15, and accelerating lenses 16 as shown in FIG. 2. The ion beam 18 having a given length and moving parallel through the ion reservoir 17 is pulsed and accelerated in a direction (Z-axis direction) perpendicular to the direction of entrance (X-axis direction) of the ion beam 18 by applying a pulsed accelerating voltage on the order of kV having the same polarity as the ions to the repeller plate 14 as shown in FIG. 2. As a result, an ion pulse 19 that starts to travel toward a reflector 8 located opposite to the ion reservoir 17 is formed.

The ions accelerated in the vertical direction have a velocity that is the sum of the X-axis direction velocity assumed when they are introduced into the measuring chamber 13 and the Z-axis direction velocity that is given perpendicularly to the X-axis direction by the ion repeller electrode, grids, and accelerating lenses. Consequently, the ions travel in a direction slightly deviating from the Z-axis direction and are reflected into the ion detector 9 by the reflector 8.

In the oa-TOFMS instrument, ions must be introduced into the ion reservoir 17 with a quite low accelerating energy. Because of this principle, it is advantageous to set the ion acceleration voltage at the ion source as low as possible. If such ion introduction at low velocity is carried out using a large amount of carrier gas ions, the ions come into contact with the ion repeller electrode 14 and grids 15 because the ions have a spatial spread. This promotes charging of these electrodes.

In the case of an oa-TOFMS instrument, mass separation is performed based on variations in arrival time at the ion detector. Therefore, the instrumental sensitivity and resolution depend on the initial position of the ions in the ion reservoir and on the uniformity of the initial kinetic energy. Accordingly, if there is nonuniform charging in the ion reservoir, the ions introduced with low acceleration have nonuniform initial position in the ion reservoir and nonuniform initial kinetic energy. Consequently, the instrumental sensitivity and resolution are deteriorated severely. Furthermore, they will age with time.

SUMMARY OF THE INVENTION

It is an object of the present invention to provide a time-of-flight mass spectrometer which has an ion source acting to massively ionize carrier gas-derived ions introduced in large quantity from a gas chromatograph and which is capable of cutting out a major portion of the carrier gas-derived ions ahead of the ion reservoir.

This object is achieved by a time-of-flight mass spectrometer which is built in accordance with the present invention and comprises: an electron impact ion source fitted with source magnets for enhancing the ionization efficiency of a sample gas; an ion reservoir for making ions produced by the ion source stay therein; an ion repeller plate and grids disposed on opposite sides of the ion reservoir to impulsively accelerate the ions out of the ion reservoir; a time-of-flight mass analyzer region for mass separating the ions extracted from the ion reservoir via the grids; and an ion detector for detecting the mass separated ions. The mass spectrometer is characterized in that it further includes first deflection means mounted between the ion source and the ion reservoir and cutoff means located between the first deflection means and the ion reservoir. The first deflection means can deflect the ions in the same direction as the direction of deflection that the ions traveling from the ion source to the ion reservoir undergo from the magnetic field produced by the source magnets. The cutoff means cuts off the deflected ions.

In one feature of the present invention, the cutoff means is a rectangular slit.

In another feature of the present invention, the cutoff means is a differentially pumped slit.

In a further feature of the present invention, the cutoff means is so constructed that a voltage can be applied to the means.

In still another feature of the present invention, second deflection means for correcting deflection of the ions induced by the source magnets and first deflection means is mounted downstream of the cutoff means.

In yet another feature of the present invention, an entrance slit for limiting the spread of the ion beam is mounted between the second deflection means and the ion reservoir.

In an additional feature of the present invention, the entrance slit has a heating mechanism.

In yet a further feature of the present invention, the sample gas is a gas supplied from a gas chromatograph.

In still a further feature of the present invention, the ions cut off are ions of a carrier gas supplied from a gas chromatograph.

Other objects and features of the present invention will appear in the course of the description thereof, which follows.

BRIEF DESCRIPTION OF THE DRAWINGS

FIG. 1 is a schematic diagram of a conventional time-of-flight (TOF) mass spectrometer;

FIG. 2 is a diagram illustrating the vicinities of the ion reservoir of the conventional TOF mass spectrometer;

DESCRIPTION OF THE PREFERRED EMBODIMENTS

Figure 3A:
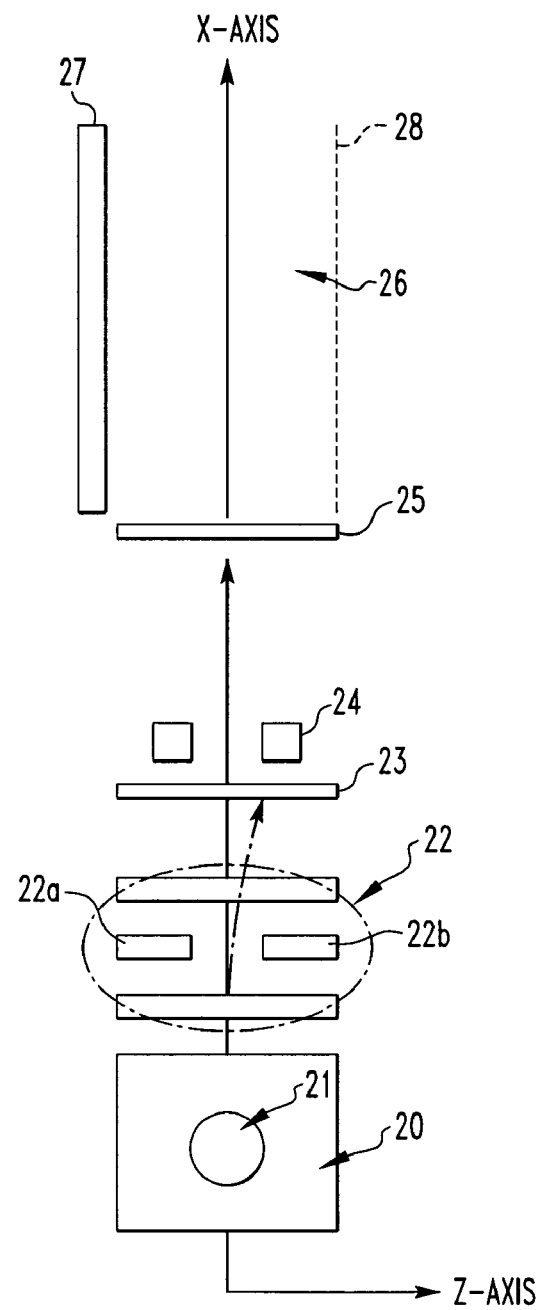
FIGS. 3(a) and 3(b) are diagrams illustrating one embodiment of the vicinities of an ion reservoir incorporated in a TOF mass spectrometer according to the present invention.
Figure 3B:
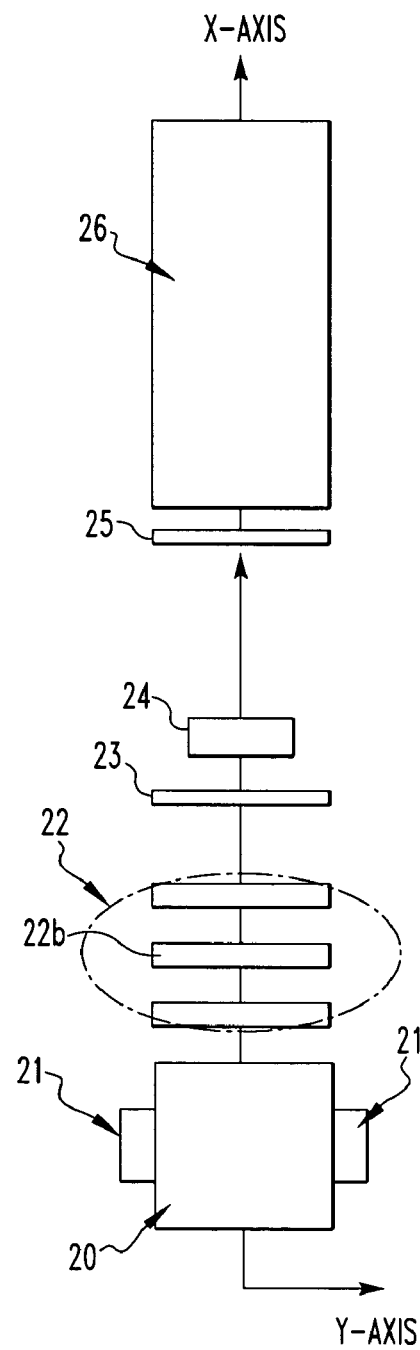

An embodiment of the present invention is hereinafter described with reference to the accompanying drawings. FIGS. 3(a) and 3(b) show one embodiment of the portion of a time-of-flight (TOF) mass spectrometer according to the invention that ranges from its ion source to the vicinity of its ion reservoir. FIG. 3(a) shows the portion from the ion source in the vicinity of the ion reservoir, as viewed from the Y-axis direction, and FIG. 3(b) shows the same portion, as viewed from the Z-axis direction.

The mass spectrometer has an ionization chamber 20 consisting of an EI ion source. In this chamber, a sample gas introduced from a gas chromatograph is ionized by thermionic emission emitted from a filament (not shown) toward the Y-axis direction. A pair of source magnets 21 is disposed on the outer wall of the ionization chamber 20 and located opposite to each other in the Y-axis direction. The main role of the source magnets 21 is to suppress the spread of the thermionic emission produced from the filament (not shown) to enhance the ionization efficiency of the sample gas. The magnets also act to deflect the produced ions in the Z-axis direction.

An electrostatic lens system 22 consisting of plural electrodes is disposed behind the ionization chamber 20. FIGS. 3(a) and 3(b) show an example in which the lens system is made up of three electrodes. At least one of the electrodes is split into two parts at the center. The two parts are located opposite to each other in the Z-axis direction and on the opposite sides of the optical axis (X-axis) of the ions. In the example of FIGS. 3(a) and 3(b), the second electrode as counted from the side of the ionization chamber 20 is split into two. The other electrodes are each centrally provided with an opening on the X-axis.

A differentially pumped slit 23 (baffle) is placed behind the system of electrostatic lenses 22 and in the partition wall that partitions the chamber in which the system of electrostatic lenses 22 is placed from the chamber in which the ion reservoir 26 is placed. A circular opening on the X-axis, a rectangular opening that is long in the Y-axis direction and short in the Z-axis direction, or an elliptical opening that is long in the Y-axis direction and short in the Z-axis direction is formed in the center of the differentially pumped slit 23.

The opening in the differentially pumped slit 23 is elongated in the Y-axis direction such that the opening extends in the same Y-axis direction along which the thermionic emission is emitted in the ion source 20. Furthermore, the opening in the slit 23 having a reduced dimension in the Z-axis direction is intended to facilitate cutting off the ions deflected in the Z-axis direction by the source magnets 21 and the split electrodes of the electrostatic lens system 22. Slits having such features are herein collectively referred to as rectangular slits.

Electrostatic deflectors 24 consisting of at least one pair of electrodes are disposed behind the differentially pumped slit 23 and opposite to each other in the Z-axis direction to correct the deflection of the ions caused in the Z-axis direction by the source magnets 21 and system of electrostatic lenses 22.

An entrance slit 25 for limiting the spread of the ion beam and the ion reservoir 26 are disposed behind the electrostatic deflectors 24. A circular opening on the X-axis, a rectangular opening that is long in the Y-axis direction and short in the Z-axis direction, or an elliptical opening that is long in the Y-axis direction and short in the Z-axis direction is formed in the center of the entrance slit 25. The ion reservoir 26 stores the ions passed through the entrance slit 25 and accelerates the ions toward the time-of-flight mass analyzer region (not shown) on the downstream side.

The instrument of the present embodiment constructed as described so far operates as follows. First, the sample gas supplied from the gas chromatograph is ionized by the thermionic emission produced in the Y-axis direction from the filament (not shown) mounted in the ionization chamber 20. Spread of the thermionic emission is suppressed by the magnetic field produced by the source magnets 21 that are located opposite to each other in the Y-axis direction on the opposite sides of the ionization chamber 20.

The produced sample ions are extracted from the ionization chamber 20 by the potential difference between the ionization chamber 20 and the system of electrostatic lenses 22. Helium ions are derived from the carrier gas in the gas chromatograph and contained in the sample ions. Ions having small masses including these helium ions are deflected to a greater extent in the Z-axis direction at this time by the magnetic field produced by the source magnets 21 than other sample ions having larger masses.

A potential difference is produced between split electrodes 22a and 22b of the system of electrostatic lenses 22, the electrodes 22a and 22b being located opposite to each other in the Z-axis direction on the opposite sides of the optical axis (X-axis) of the ions. This promotes the deflection in the same direction as the direction of deflection produced by the magnetic field of the source magnets 21.

For this purpose, in a case where the produced ions are positive ions and the axis of the ion beam is deflected toward the split electrode 22a by the source magnets 21, the split electrode 22a is placed at a lower potential than the split electrode 22b.

Furthermore, in a case where the produced ions are positive ions and the axis of the ion beam is deflected toward the split electrode 22b by the source magnets 21, the split electrode 22b is placed at a lower potential than the split electrode 22a.

Where the produced ions are negative ions and the axis of the ion beam is deflected toward the split electrode 22a by the source magnets 21, the split electrode 22a is placed at a higher potential than the split electrode 22b.

Where the produced ions are negative ions and the axis of the ion beam is deflected toward the split electrode 22b by the source magnets 21, the split electrode 22b is placed at a higher potential than the split electrode 22a.

Of the ions deflected by the source magnets 21 and the split electrodes 22a and 22b of the system of electrostatic lenses 22, helium ions and other ions having small masses are deflected to a greater extent. These lighter ions collide against the wall of the differentially pumped slit 23 and thus are cut off. Hence, these lighter ions cannot reach the downstream ion reservoir 26.

On the other hand, those of the sample ions deflected by the split electrodes 22a and 22b of the system of electrostatic lenses 22 which are deflected to a lesser extent and have larger masses pass through the opening in the differentially pumped slit 23 and then are corrected in terms of deflection by the downstream electrostatic deflectors 24 consisting of at least one pair of electrodes located opposite to each other in the Z-axis direction such that the Z-axis direction deflection of the ion beam caused by the source magnets 21 and split electrodes 22a, 22b of the electrostatic lenses 22 agrees in direction with the optical axis (X-axis) of the ion reservoir 26.

The sample ions corrected in terms of ion beam axis are restricted in ion spread by the entrance slit 25 and introduced into the ion reservoir 26. Then, the ions are accelerated toward the grids 28 (i.e., in the Z-axis direction) by applying a high pulsed voltage of hundreds of volts to kilovolts having the same polarity as the ions to the ion repeller plate 27. The ions travel through the time-of-flight mass analyzer region (not shown) and reach the ion detector (not shown), where they are detected.

FIGS. 4(a), 4(b), 4(c), and 4(d) are mass spectra observed in a case where the same value of voltage is applied to the electrostatic lens electrodes 22a and 22b bisected in the Z-axis direction such that no potential difference is produced between them and in another case where different values of voltage are applied to the electrodes to produce a potential difference between them, respectively.

Figure 4A:
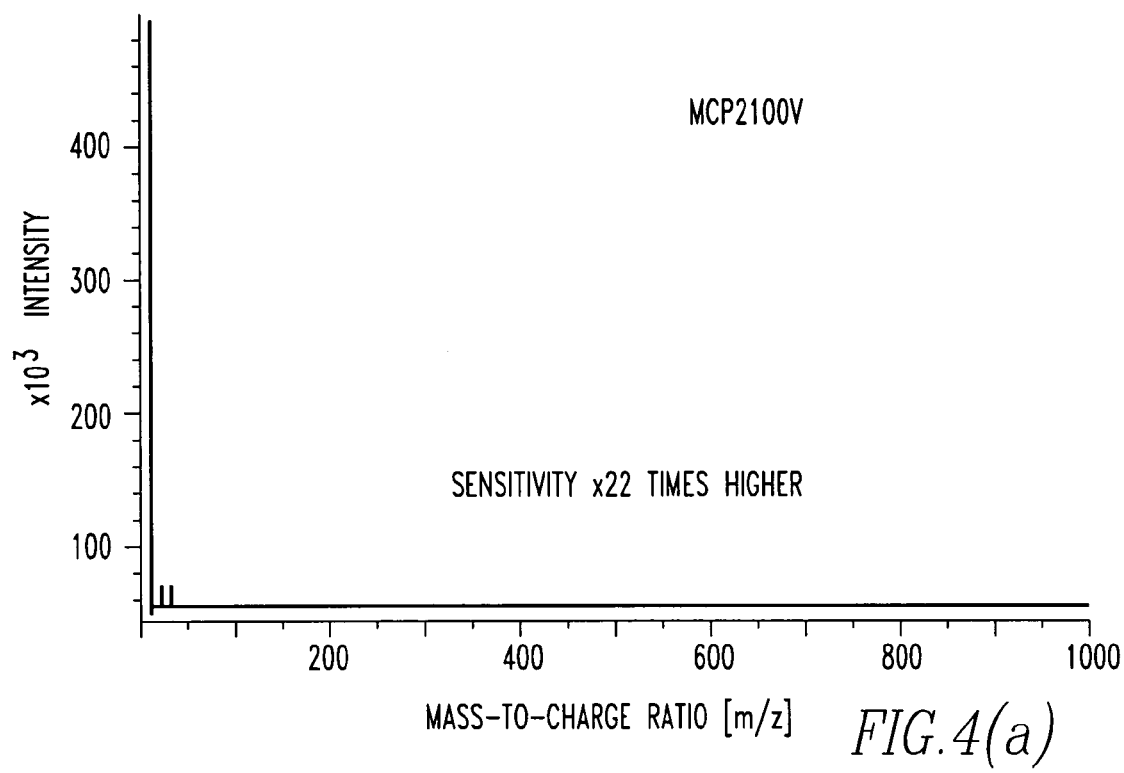
FIGS. 4(a), 4(b), 4(c), and 4(d) show mass spectra measured using the present invention.
Figure 4B:
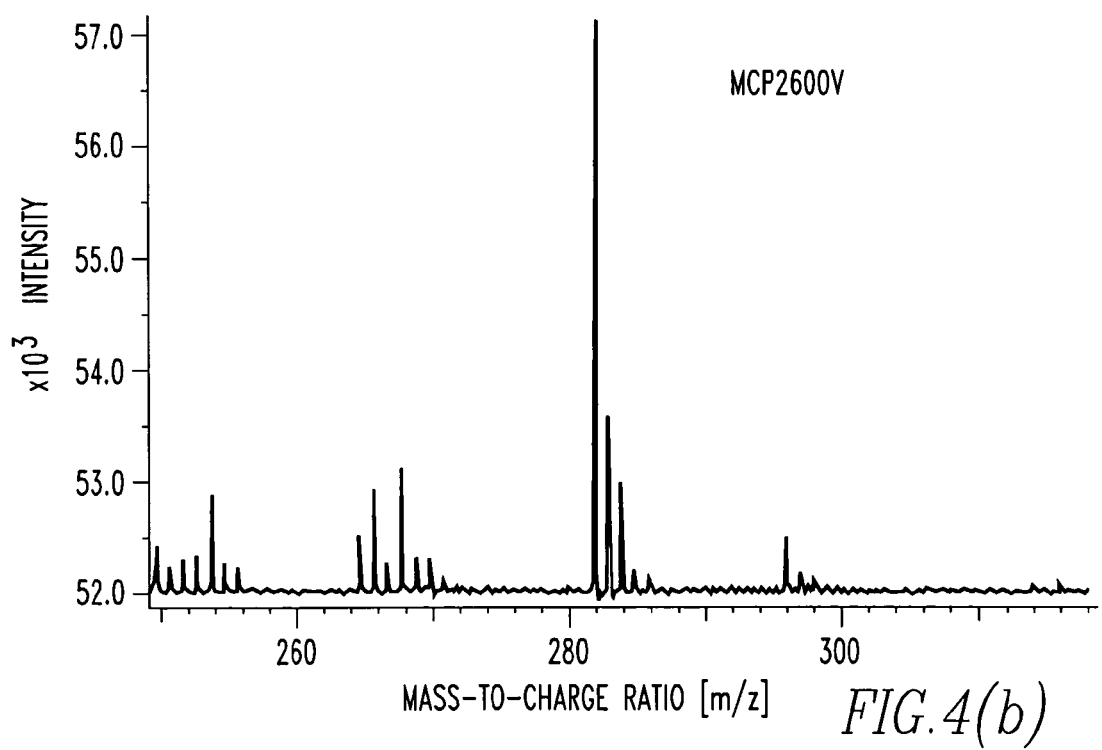
Figure 4C:
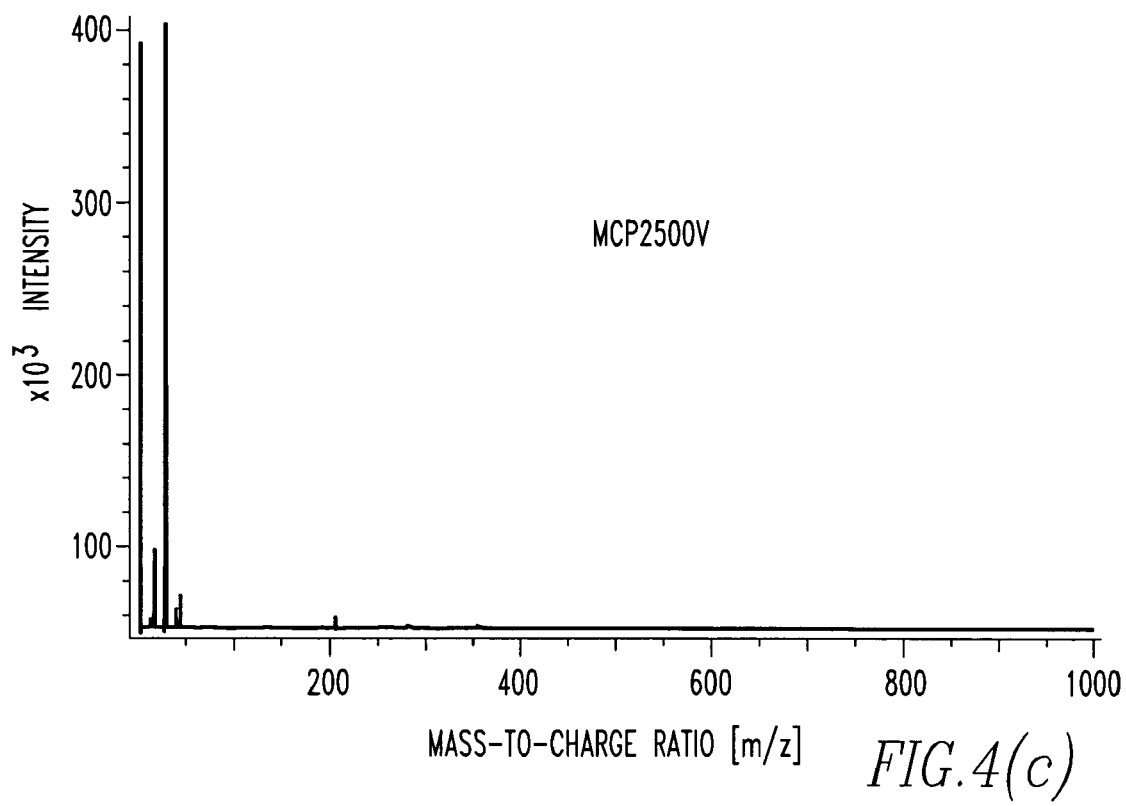
Figure 4D:
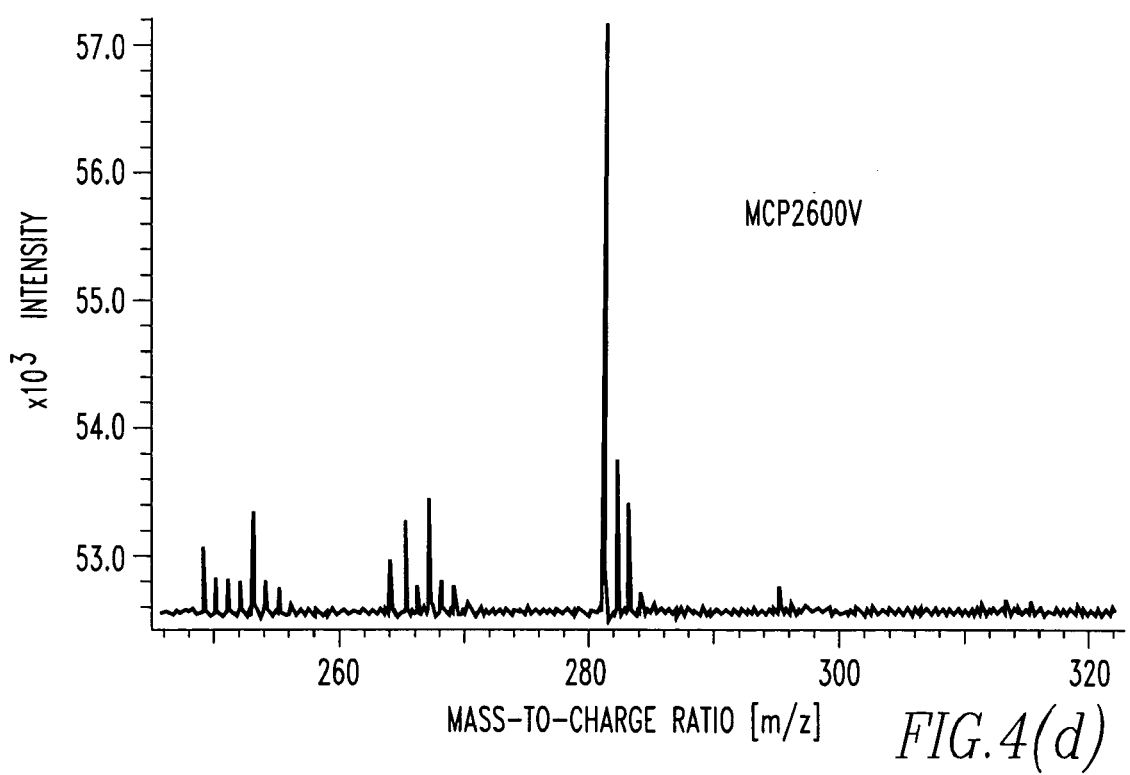

FIGS. 4(a) and 4(b) show the mass spectra obtained where the same value of voltage is applied to the electrostatic lens electrodes 22a and 22b bisected in the Z-axis direction such that no potential difference is produced between them. FIGS. 4(c) and 4(d) show the mass spectra obtained where different values of voltage are applied to the electrodes to produce a potential difference between them.

Also in FIGS. 4(a) and 4(c) are the mass spectra derived by noting helium ions (m/z =4). FIGS. 4(b) and 4(d) are mass spectra derived by noting the peak (m/z=281) derived from the column's stationary phase. (Hereafter, the mass spectra are referred to as (a), (b), (c), and (d).)

With respect to these mass spectra, the MCP (detector) voltage that determines the sensitivity of the detector (MCP) has different values of 2.1 kV, 2.6 kV, 2.5 kV, and 2.6 kV for spectra (a), (b), (c), and (d), respectively. Therefore, the sensitivity is not uniform. The relation between the MCP voltage and sensitivity (ion intensity) is given by

| MCP voltage | Sensitivity |
|---|---|
| 2.1 kV | 1 |
| 2.5 kV | 22 |
| 2.6 kV | 37 |

In each of the mass spectra (a) and (c), the left end peak indicates helium ions. In these mass spectra, the peak intensities of the helium ions are $441 \times 10^3$ (MCP voltage: 2.1 kV)

$347 \times 10^3$ (MCP voltage: 2.5 kV), respectively.

By taking account of the difference in MCP sensitivity, a potential difference is produced between the electrostatic lens electrodes 22a and 22b. As a result, 96% of the helium ions can be cut out.

Comparison of the mass spectra (b) and (d) reveals that the mass resolution has been improved by a factor of about 1.5 compared with the conventional TOFMS instrument.

It is to be noted that various changes and modifications are possible in the present invention. For example, the differentially pumped slit 23 may be made of an electrode to which a voltage can be applied. This can cancel the effects of charging that would normally be produced by causing a collision of helium ions and cutting them off.

Furthermore, the entrance slit 25 may be provided with a heating mechanism. Adhesion of contaminants to the entrance slit 25 is prevented by heating the slit 25. Consequently, the slit can be operated stably for a long time.

The present invention makes it possible to cut out a major portion of carrier gas-derived ions ahead of the ion reservoir, it being noted that the carrier gas-derived ions are introduced in large quantity from a gas chromatograph and will be ionized in large quantity in the ion source.

Having thus described our invention with the detail and particularity required by the Patent Laws, what is desired protected by Letters Patent is set forth in the following claims.

The invention claimed is:

1. A time-of-flight mass spectrometer comprising:
   an electron impact ion source fitted with source magnets for enhancing the efficiency at which sample gas is ionized;
   an ion reservoir for gathering ions produced in said ion source, wherein said ions travel from said ion source to said ion reservoir along an axis;
   an ion repeller plate and grids disposed on opposite sides of the ion reservoir to impulsively accelerate the ions out of the reservoir;
   a time-of-flight mass analyzer region for mass separating the ions extracted from the ion reservoir via the grids;
   an ion detector for detecting the mass separated ions;
   first deflection means mounted between the ion source and the ion reservoir for deflecting the ions in a direction generally perpendicular to said axis and in the same direction as the direction of deflection that the ions traveling from the ion source to the ion reservoir undergo from a magnetic field produced by the source magnets; and
   cutoff means located between the first deflection means and the ions reservoir to cut off the deflected ions.

2. A time-of-flight mass spectrometer as set forth in claim 1, wherein said cutoff means is a rectangular slit.

3. A time-of-flight mass spectrometer as set forth in claim 1, wherein said cutoff means is a differentially pumped slit.

4. A time-of-flight mass spectrometer as set forth in claim 1, wherein said cutoff means is so constructed that a voltage can be applied thereto.

5. A time-of-flight mass spectrometer as set forth in claim 1, wherein at least one pair of second deflection means for correcting deflection of the ions caused by said source magnets and said first deflection means being mounted between said cutoff means and said ion reservoir.

6. A time-of-flight mass spectrometer as set forth in claim 5, wherein there is provided an entrance slit between said second deflection means and said ion reservoir to restrict spread of a beam of the ions.

7. A time-of-flight mass spectrometer as set forth in claim 6, wherein said entrance slit is fitted with a heating mechanism.

8. A time-of-flight mass spectrometer as set forth in claim 1, wherein said sample gas is a gas supplied from a gas chromatograph.

9. A time-of-flight mass spectrometer as set forth in claim 1, wherein said ions cut off are ions of a carrier gas supplied from a gas chromatograph.

* * * * *

UNITED STATES PATENT AND TRADEMARK OFFICE
CERTIFICATE OF CORRECTION

PATENT NO. : 7,034,288 B2  Page 1 of 1
APPLICATION NO. : 10/877497
DATED : April 25, 2006
INVENTOR(S) : Satoh et al.

It is certified that error appears in the above-identified patent and that said Letters Patent is hereby corrected as shown below:

On the title page:
   Item (30)    Foreign Application Priority Data
   June 26, 2003              (JP) .............. 2003-182468

<u>Column 8</u>, line 11, Claim 1, "of the reservoir" should read -- of the ion reservoir --

<u>Column 8</u>, line 23, Claim 1, "ions reservoir" should read -- ion reservoir --

Signed and Sealed this

Twenty-sixth Day of September, 2006

JON W. DUDAS
*Director of the United States Patent and Trademark Office*